US006572534B1

(12) United States Patent
Milbocker et al.

(10) Patent No.: US 6,572,534 B1
(45) Date of Patent: Jun. 3, 2003

(54) SYSTEM AND METHOD FOR IMPLANTING A CARDIAC WRAP

(75) Inventors: Michael T. Milbocker, Holliston, MA (US); Robert L. Buck, Methuen, MA (US)

(73) Assignee: Abiomed, Inc., Danvers, MA (US)

( * ) Notice: Subject to any disclaimer, the term of this patent is extended or adjusted under 35 U.S.C. 154(b) by 0 days.

(21) Appl. No.: 09/661,624

(22) Filed: Sep. 14, 2000

(51) Int. Cl.[7] ................................................. A61F 2/02

(52) U.S. Cl. ............................................ 600/37; 600/16

(58) Field of Search ............................... 600/16–18, 37; 601/151–153; 623/3.1

(56) References Cited

U.S. PATENT DOCUMENTS

| 2,826,193 A | 3/1958 | Vineberg |
| 3,464,322 A | 9/1969 | Pequignot |
| 3,587,567 A | 6/1971 | Schiff |

(List continued on next page.)

FOREIGN PATENT DOCUMENTS

| EP | 0370931 A1 | 5/1990 |
| GB | 2115287 A | 9/1983 |
| JP | 2271829 | 11/1990 |
| SU | 1009457 A | 7/1983 |
| SU | 1734767 A1 | 5/1992 |
| WO | WO 94/21237 | 9/1994 |
| WO | WO 99/22784 | 5/1999 |

OTHER PUBLICATIONS

Anstadt, George L., Blakemore, W.S., Baue, A.E. "A New Instrument for Prolonged Mechanical Cardiac Massage." Circulation. 1965. vol. 31 and 32, Supplement II, II 43–II–44. Lippincott Williams & Wilkins.

Vaynblat, Mikhail et al. "Cardiac Binding in Experimental Heart Failure." Ann. Thorac. Surg. 1997. 64:81–85. Elsevier Science Inc.

Vaynblat, Mikhail et al. "Cardiac Binding in Experimental Heart Failure." Circulation. 1995. 92(8) :I–380. Lippincott Williams & Wilkins.

Chekanov, Valeri. "Nonstimulated Cardiomyoplasty Wrap Attenuated the Degree of Left Ventricular Enlargement." Ann. Thorac. Surg. 1994. 57:1684–1685. Elsevier Science Inc.

Kass, David A. et al. "Reverse Remodeling from Cardiomyoplasty in Human Heart Failure: External Constraint Versus Active Versus Active Assist." Circulation. 1995. 91(9) :2314–2318. Lippincott Williams & Wilkins.

Carpentier, A., Chachques J.C. "Myocardial Substitution with a Stimulated Skeletal Muscle: First Successful Clinical Case." The Lancet. 1985. 1:1267. The Lancet Publishing Group.

Anstadt, Mark P. Anstadt, George L., Lowe, James E. "Direct Mechanical Ventricular Actuation: A Review." Resuscitation. 1991. 21:7–23. Elsevier Science Inc.

Anstadt, Mark P., Stonningham. Michael J., Tedder, Mark, Crain, Barbara J., Menius, J. Alan, Lowe, James E. "Pulsatile Reperfusion After Cardiac Arrest Improves Neurologic Outcome." Annals of Surgery. 1991. 214(4):478–490. American Surgical Association.

(List continued on next page.)

*Primary Examiner*—Max F. Hindenburg
*Assistant Examiner*—Joseph A. Cadugan
(74) *Attorney, Agent, or Firm*—Thomas J. Engellenner; Geoffrey S. Smith; Nutter McClennen & Fish LLP

(57) ABSTRACT

A system and method for implanting a wrap on a patient's heart or other organ provides a wrap having finger-engagement members typically defining loops that encompass all or a substantial portion of the fingers of a surgeon's treatment hand. The loops retain the fingers to the wrap during implant, and enable the fingers to be detached after the procedure is complete. The loops can be detachable from the wrap after the procedure is completed or can be formed to remain with the wrap.

49 Claims, 14 Drawing Sheets

U.S. PATENT DOCUMENTS

| | | | |
|---|---|---|---|
| 3,613,672 A | | 10/1971 | Schiff |
| 3,659,593 A | | 5/1972 | Vail |
| 3,674,019 A | | 7/1972 | Grant |
| 4,157,713 A | | 6/1979 | Clarey |
| 4,340,091 A | | 7/1982 | Skelton et al. |
| 4,536,893 A | | 8/1985 | Parravicini |
| 4,628,937 A | | 12/1986 | Hess et al. |
| 4,690,134 A | | 9/1987 | Snyders |
| 4,803,744 A | | 2/1989 | Peck et al. |
| 4,827,932 A | | 5/1989 | Ideker et al. |
| 4,902,291 A | | 2/1990 | Kolff |
| 4,936,857 A | | 6/1990 | Kulik |
| 4,957,477 A | | 9/1990 | Lundback |
| 5,078,134 A | | 1/1992 | Heilman et al. |
| 5,098,369 A | | 3/1992 | Heilman et al. |
| 5,111,818 A | | 5/1992 | Suzuki et al. |
| 5,119,804 A | | 6/1992 | Anstadt |
| 5,131,905 A | | 7/1992 | Grooters |
| 5,150,706 A | * | 9/1992 | Cox et al. .................... 128/897 |
| 5,169,381 A | | 12/1992 | Snyders |
| 5,243,723 A | | 9/1993 | Cotner et al. |
| 5,336,254 A | | 8/1994 | Brennen et al. |
| 5,383,840 A | | 1/1995 | Heilman et al. |
| 5,534,024 A | | 7/1996 | Rogers et al. |
| 5,558,617 A | | 9/1996 | Heilman et al. |
| 5,564,142 A | | 10/1996 | Liu |
| 5,611,085 A | | 3/1997 | Rasmussen |
| 5,702,343 A | | 12/1997 | Alferness |
| 5,704,891 A | | 1/1998 | Mussivand |
| 5,707,336 A | | 1/1998 | Rubin |
| 5,713,954 A | | 2/1998 | Rosenberg et al. |
| 5,741,316 A | | 4/1998 | Chen et al. |
| 5,800,528 A | | 9/1998 | Lederman et al. |
| 5,853,005 A | | 12/1998 | Scanlon |
| 5,902,229 A | | 5/1999 | Tsitlik et al. |
| 5,971,910 A | | 10/1999 | Tsitlik et al. |
| 5,991,665 A | | 11/1999 | Wang et al. |
| 5,991,925 A | | 11/1999 | Wu |
| 6,065,154 A | | 5/2000 | Hulings et al. |
| 6,076,013 A | | 6/2000 | Brennan et al. |
| 6,179,793 B1 | | 1/2001 | Rothman et al. |
| 6,179,800 B1 | | 1/2001 | Torrens |
| 6,212,430 B1 | | 4/2001 | Kung |
| 6,221,103 B1 | | 4/2001 | Melvin |
| 6,251,061 B1 | * | 6/2001 | Hastings et al. .............. 600/16 |
| 6,260,552 B1 | * | 7/2001 | Mortier et al. .............. 128/898 |

OTHER PUBLICATIONS

Bencini, Adriano., Parola, Pier L. "The 'Pneumomassage' of the Heart." Surgery. 1956. 39:375–384. The National Medical Society.

Capouya, Eli R. et al. "Girdling Effect of Nonstimulated Cardiomyoplasty on Left Ventricular Function." Ann. Thorac. Surg. 1993. 56:867–71. Elsevier Science Inc.

Carpentier, Alain et al. "Dynamic Cardiomyoplasty at Seven Years." The Journal of Thoracic and Cardiovascular Surgery. 1993. 106(1) :42–54. Mosby, Inc.

Article "Tissue Engineering" Robert Langer and Joseph P. Vancanti; Science, vol. 260, May 14, 1993; pp. 920–926.

Article "Biodegradable Polymer Scaffolds for Tissue Engineering" Lisa E. Freed; Gordan Vanjak–Novakovic; Robert J. Biron; Dana B. Eagles; Daniel C. Lesnoy; Sandra K. Barlow and Robert Langer; Bio/Tecnology vol. 12, Jul. 1994; pp. 689–693.

* cited by examiner

SYSTEM AND METHOD FOR IMPLANTING A CARDIAC WRAP

RELATED PATENTS

This application is related to U.S. Pat. Nos. 5,713,954 and 5,800,528, both expressly incorporated herein by reference.

BACKGROUND OF THE INVENTION

1. Field of the Invention

This invention relates to wraps for internal organs and methods for implanting such devices on a patient's affected region through an incision in the patient's thoracic region, and more particularly to cardiac wraps and methods for implanting such wraps.

2. Background Information

Ventricular dilation is clinically dangerous condition in which a ventricle of the patient's heart enlarges in radius (e.g. dilates) until it is incapable of adequately pumping necessary blood through the patient's body. A number of invasive procedures have been employed through the years in an effort to remedy ventricular dilation and other progressive diseases that bring about a weakened heart. Many of these procedures involve the use of cardiac treatment devices that are implanted through the wall of the heart, and thereby come into direct contact with the bloodstream and internal vascular tissue. One potential downside to such internally implanted devices is that continuing risk of clotting or thrombosis around the device, and possible thromboembolism. This risk is present whenever artificial materials are used, causing the accretion thereon of blood components. These risks are typically controlled, or at least reduced through the application of ongoing anticoagulant therapy. Such anticoagulants have several undesirable side effects, however.

Improved therapies and associated devices now exist that, for certain conditions, alleviate the need for internally implanted devices that directly contact the bloodstream. Ventricular dilation is a condition that can be effectively treated using implants that are essentially free of contact with the heart's internal, blood-contacting surfaces. U.S. Pat. No. 5,800,528, entitled PASSIVE GIRDLE FOR HEART VENTRICLE FOR THERAPEUTIC AID TO PATIENTS HAVING VENTRICULAR DILATION by Lederman et al., expressly incorporated herein by reference, teaches one such treatment device. The exemplary device defines a cup-like girdle that is passed through an enlarged incision in the chest cavity and onto the ventricular region of the heart, remote from the major blood vessels. The device is passed over the affected ventricle or both affected ventricles by the clinician/surgeon using clamps for gripping the device, moving the device until it is properly seated on the ventricle. Once seated, it is held in place by small internal hooks (microhooks) or other fastening devices (sutures) that engage the outer wall of the heart. The girdle can be further constricted to compress the dilated ventricle using various mechanical systems such as pneumatic/hydraulic balloons or drawstrings. In this manner, the compression of the girdle passively (and continuously) counteracts excessive dilation of the ventricle.

U.S. Pat. No. 5,713,954, entitled EXTRA CARDIAC VENTRICULAR ASSIST DEVICE by Rosenberg et al., also expressly incorporated herein by reference, teaches an active device that dynamically assists in the actual pumping of blood by the ventricle. This device is, like the girdle, applied through an enlarged incision in the thoracic region, and secured to the ventricle. A hydraulic or pneumatic control system enables internal balloons within the device to repetitively inflate and deflate, respectively constricting and expanding the ventricle.

Both the above-described exemplary devices each employ an element termed a "wrap" that essentially wraps around the ventricular region of the heart. The implantation of the wrap typically requires a fairly large incision in the chest cavity, and a significant degree of manipulation by the surgeon, often using both hands and with the assistance of various clamps and the like.

As the implantation of the above-described devices often entails the use of various mechanical tools for grasping and handling the device with respect to the heart the surgeon's tactile feedback in applying the device is reduced and, hence, his or her control over the implantation is reduced. However, it is crucial for maximum therapeutic effect that the device be properly fitted to the specific conforms of the heart and placed "high" enough of the ventricle (e.g. toward the major blood vessels) so that the device applies compression to the upper part of the ventricle where it is needed most. With less tactile feedback on the shape of the heart and relative location of the device, it is more difficult to ensure proper implantation, and take more procedure time to perform the implantation.

Accordingly, it is an object of this invention to provide a system and method for applying wrap that enables easier manipulation onto, and fixation to, the affected region of a patient's heart. The wrap should be easily manipulable by one hand and arranged to enable accurate implantation onto the affected region with reduced effort. A smaller incision between the patient's ribs (e.g. a thoracotomy), should be possible using this system and method. The system and method of this invention should generally provide the surgeon with greater control and tactile feedback during the procedure, thus enabling a quicker and more-effective placement of the device.

SUMMARY OF THE INVENTION

This invention overcomes the disadvantages of the prior art by providing a system and method for implanting a wrap on a patient's heart, or other organ, that enables the clinician/surgeon to manipulate and apply the wrap to the affected with a single hand, maintaining the wrap in positive engagement with this treatment hand until detachment of the hand from the wrap is desired. To accomplish this, the wrap is provided with one or more engagement members that retain respective fingers of the surgeon's hand, or other manipulator, with respect to the wrap. The engagement members enable ready release of the surgeon's hand or other manipulator from the wrap, at a predetermined detachment time after it has been properly located relative to the heart's affected region and secured in an appropriate orientation thereon. The engagement members essentially allow selected fingers of the treatment hand to act as direct clamps for the wrap while providing close tactile feedback as the surgeon feels the underlying heart.

In a preferred embodiment, the engagement members comprise loop members that encircle all or a substantial portion of the selected fingers. The loop members can be attached to the wrap so that the surgeon's fingers engage respective loop members during wrap implantation, and can be withdrawn from the loop members after implantation is complete. Typically, the loop members are disposed about a circumference of the wrap at predetermined circumferential locations, near the distal end of the wrap so that the selected fingers can wrap around the patient's heart to manipulate the wrap thereover. In one embodiment related to a wrap with opposing free ends, the loop members are arranged so that four fingers are engaged thereby, while the thumb remains free to hold opposing free ends of the wrap in place over the heart while the free ends are joined together in an overlapping relationship to achieve a desired circumference and angular shape with respect to the affected ventricle(s).

In an alternate embodiment, the loop members can be removeably attached to the wrap using hooks, pins or other suitable attachment mechanisms. After fixation of the wrap to the patient's heart is completed, the loop members are themselves withdrawn by the surgeon. In another alternate embodiment, the removable loop members can comprise the ends of a special surgeon's glove that selectively and removably engage locations on the wrap.

The wrap having engagement members according to this invention can be either a closed cup or tube having a predetermined circumference profile/geometry arranged to fit over the ventricular portion of the heart and be compressed into a final shape thereon. Alternatively, the wrap can be an open strip of material that is wrapped around the ventricular region of the heart and subsequently secured to it to thereby provide desired compression to the ventricular region.

BRIEF DESCRIPTION OF THE DRAWINGS

The foregoing and other objects and advantages of the invention will become clearer with reference to the following detailed description as illustrated by the drawings in which.

DETAILED DESCRIPTION OF ILLUSTRATIVE EMBODIMENTS

Figure 1:
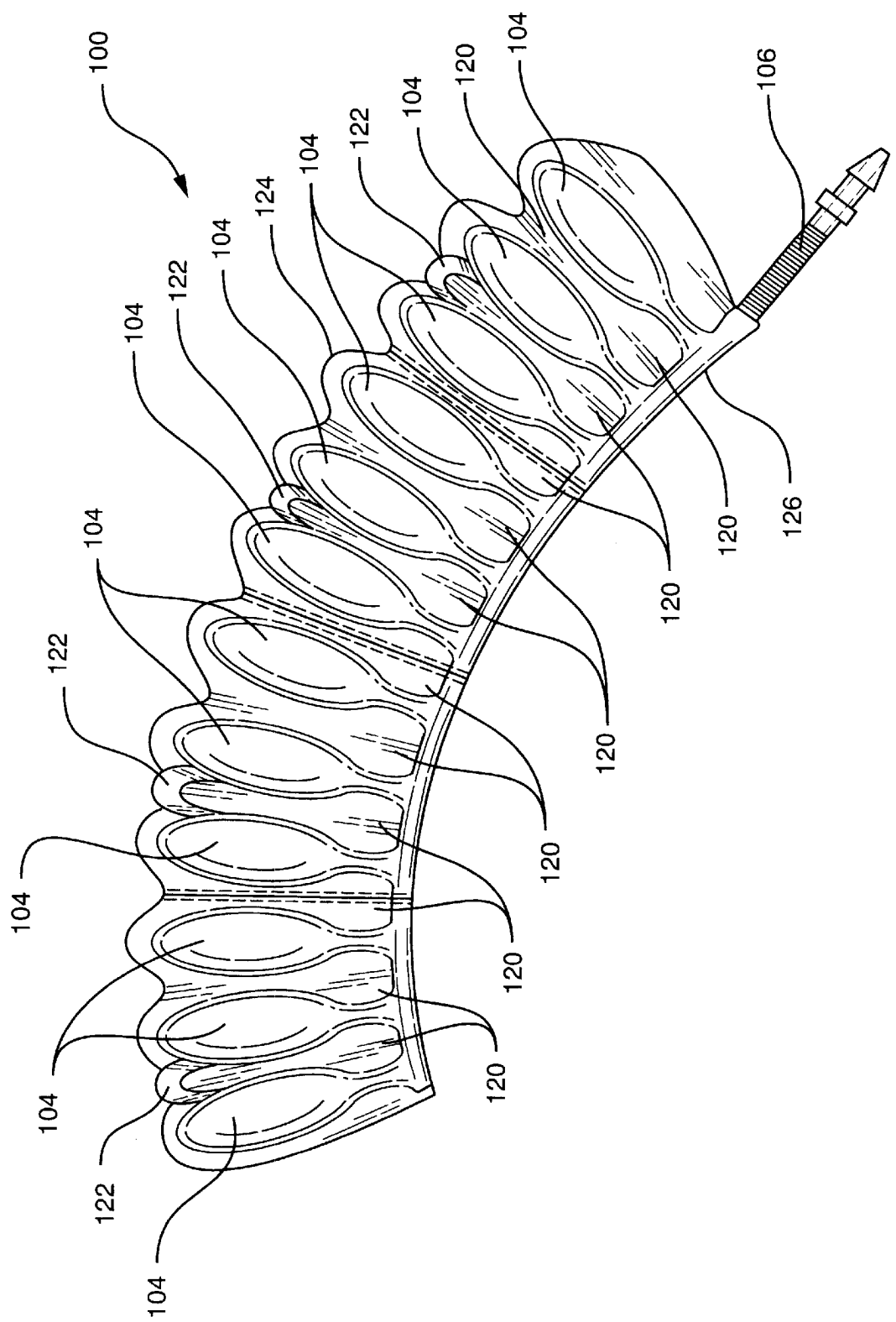
FIG. 1 is a plan view of a cardiac wrap having engagement members for assisting a surgeon in implantation according to a preferred embodiment of this invention.
Figure 2:
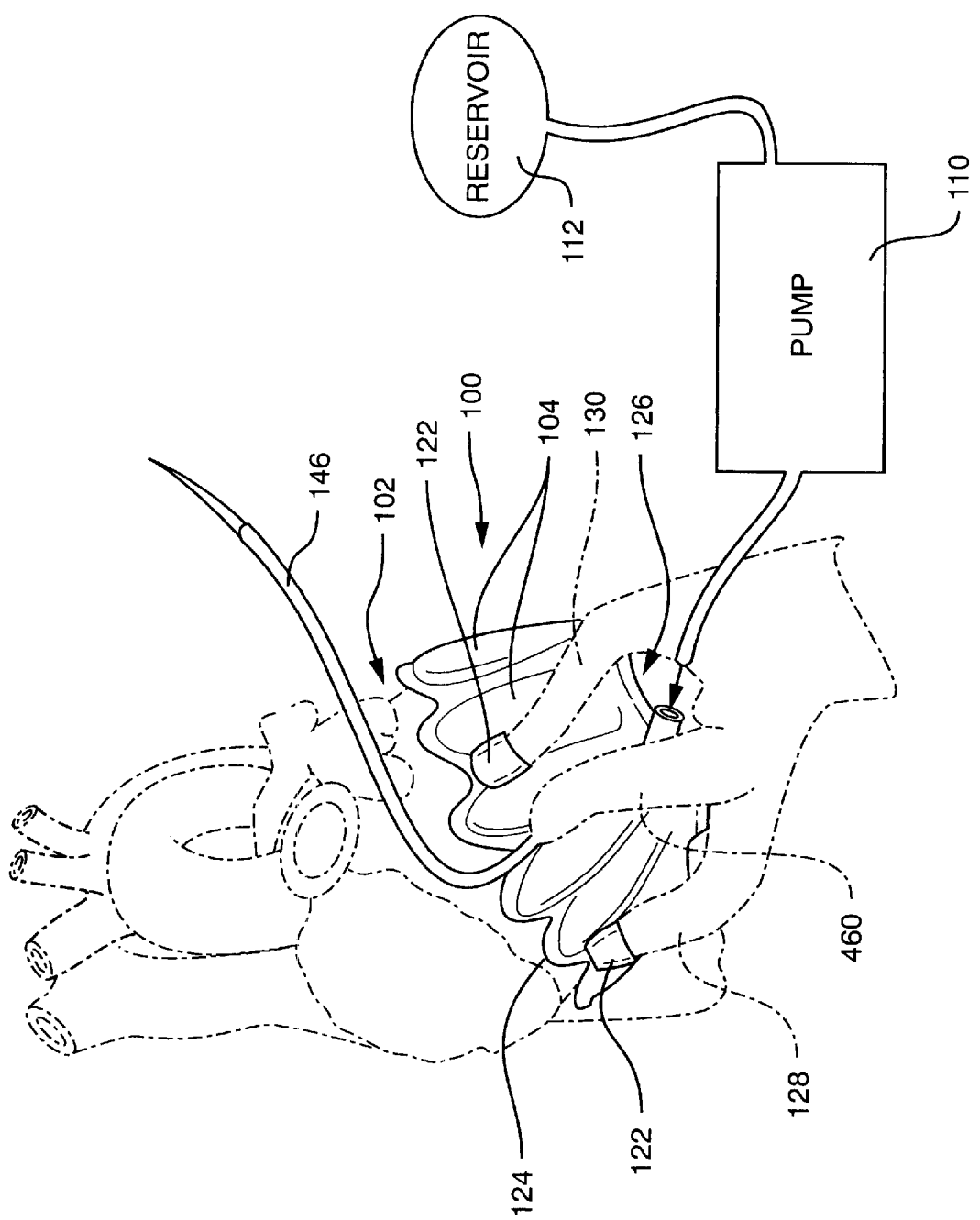
FIG. 2 is a perspective view of the wrap applied to an exemplary heart ventricle.

FIG. 1 illustrates a cardiac wrap according to a preferred embodiment of this invention. The illustrated wrap is part of an extra-cardiac ventricular assist device, which includes attached pumping and control mechanisms. The wrap 100 is adapted to "wrap" around the ventricular portion of the heart to apply pressure to the ventricles. This relationship is shown generally in FIG. 2 in which the wrap 100 is placed on an exemplary heart 102. As described further below, the principles of this invention are applicable to a variety of devices for engaging, and encompassing a portion of the heart, or another organ. These devices will be generally termed "wraps" for the purpose of this description. In fact, such devices, as described herein, can include active devices, that expand and contract with respect to the heart, and passive devices that prevent continued dilation of the heart. In addition, these devices can be open prior to implantation (such as the wrap of FIG. 1), with opposing free ends; or closed (refer generally to FIG. 8) with a distal opening of predetermined diameter that is passed over the affected region of the heart. The opposing, proximal end of this closed device can be either closed or open, typically with a diameter smaller than the diameter of the distal opening.

The wrap 100 of FIG. 1 is an active type that includes a series of balloons 104 installed within fabric pockets and interconnected to one or more pressure lines 106. A pump (110 in FIG. 2) can fill and deflate the balloons within each of the pockets using a gas or liquid stored in a reservoir 112 (see FIG. 2). The wrap of this and other embodiments described herein is constructed from a biocompatable material such as woven polytetrafluroethylene (PTFE) fabric. In general, the fabric should be pliable, but exhibit minimal extensibility (typically non-distensible) for accurate application of pressure. In other words, the fabric should be relatively free of give, when it is wrapped around the heart. The wrap of FIG. 1 is constructed from two plies of fabric that define the balloon pockets 104 and interstitial sections 120 between the pockets 104. The fabric is drawn into closely overlaid pair of layers within the interstitial sections 120. The number of balloon pockets 104 and corresponding balloons is variable. Twelve balloon pockets are used on an exemplary wrap that defines an open length of between eleven and eighteen inches (thereby defining an eleven to eighteen-inch circumference). This is a size range generally applicable to an adult human heart. The various seams of the wrap in this and other embodiments can be constructed using stitching with an appropriate biocompatable thread. Alternatively, welding, adhering with adhesives or a combination of joining techniques can be employed to form the wrap.

Located at desired intervals along the wrap are finger engagement members 122 according to a preferred embodiment. These engagement members or "loop members" 122 essentially define loops/loop elements of biocompatible material located at the interstitial locations 120 between balloon pockets 104. They can alternatively be referred to as "finger cots" in certain embodiments—particularly where they cover a portion of the finger. However, the term "loop member(s)" shall be used herein the describe generally any structure/finger engagement member that encompasses all or a substantial portion a finger's circumference so as to firmly engage the finger, free of unwanted detachment. The loop members 122 are positioned near the distal ends 124 of the wrap opposite the proximal end 126 that resides near the ventricular region of the heart when the wrap is applied thereto. As detailed in FIG. 2, the loop members 122 engage portions of the fingers 128, 130 of the surgeon's treatment hand. Briefly, the loop members 122 enable the surgeon to retain a positive grip on the wrap as it is inserted through an incision in the patient and over the ventricular region of the heart. The loop members, furthermore, enable the surgeon to accurately manipulate the wrap into an optimal position over the desired ventricle.

Figure 3:
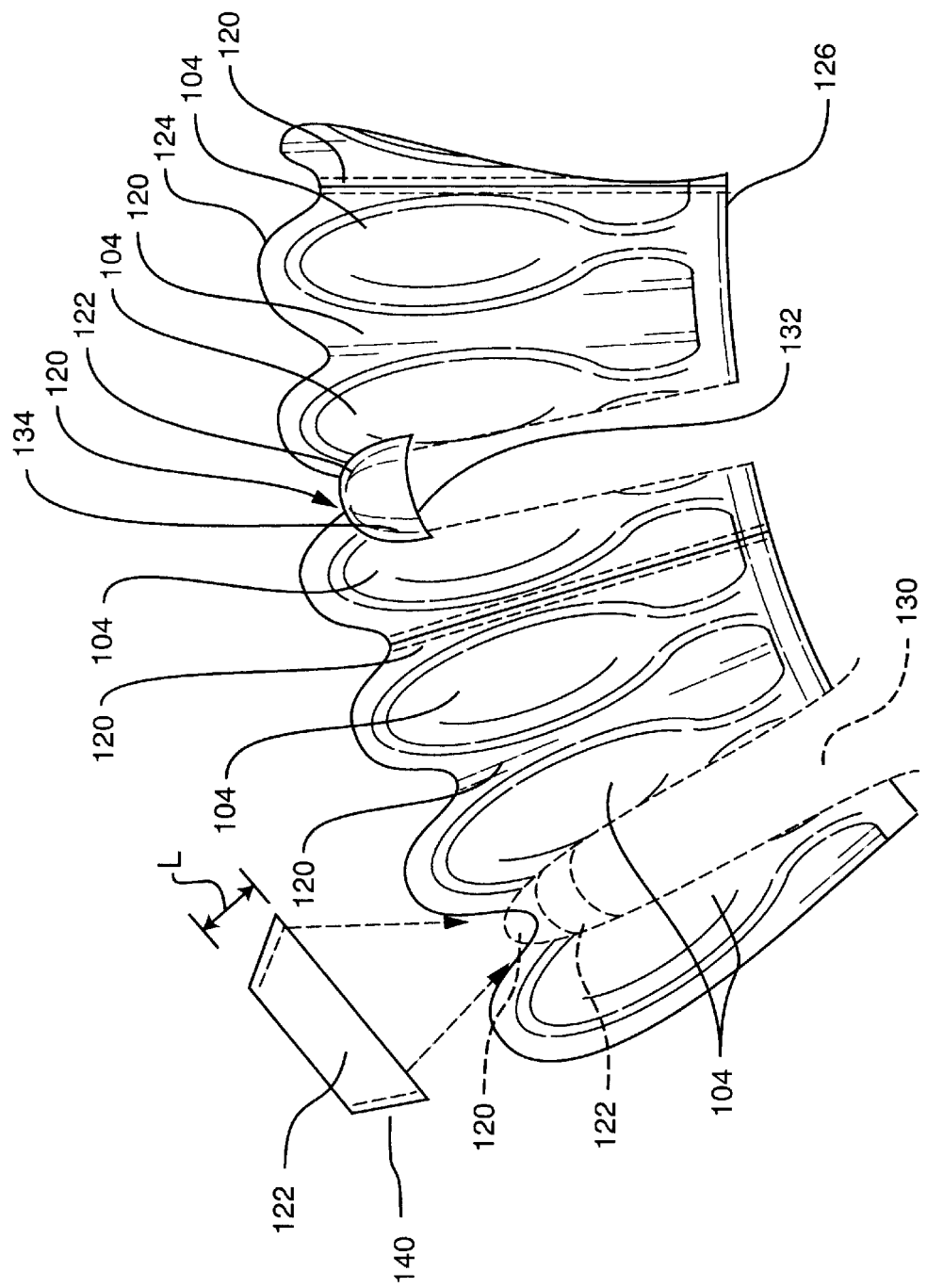
FIG. 3 is a partial plan view showing a portion of the wrap of FIG. 1 in further detail.

The loop members 122 are shown in greater detail in FIG. 3. In this embodiment, they are open loops. In other words, they define both a proximal opening 132 facing the proximal end 126 of the wrap and a distal opening 134 facing the distal end 124 of the wrap. According to this embodiment, each loop member 122 defines a trapezoidal shape so that the loop tapers inwardly from the wider proximal opening 132 to the narrower distal opening 134. This enables the surgeon's fingers to become firmly engaged on the tapering loops at a given point along their length L in which the thickness of the surgeon's finger approximately matches inner diameter of the loop. The length L is highly variable, but it is typically at least a ¾ inch in length to cover a sufficient portion of the finger so that appropriate control of the wrap can be maintained. Again, this parameter can be varied significantly depending upon the size shape and configuration of the wrap. As will be described further below, the positioning of loop members on wrap can also be varied widely. In this embodiment, loop members are disposed between each three balloon pockets 104 so as to define an even spacing for four loop members. However, greater or fewer members can be applied to the surface of the wrap allowing the surgeon to select different gripping locations where appropriate. Typically, the thumb is left free in this embodiment for reasons described further below. Also the illustrated loop members are placed near the distal end of the wrap so that firm control of the upper end of the device can be maintained and "high" placement of the device on a ventricle can be achieved. Placement along the proximal-to-distal direction can be varied.

As shown in FIG. 3, the loop member 122 is attached to the interstitial section 120 using stitches 140 of an appropriate biocompatible thread. A variety of attachment techniques can be utilized including clips, welding adhesive, etc. The loop member is also composed of biocompatible material having a certain desired properties. For example, the interior of the loop member can include a rough friction-generating surface or the loop member can be constructed from a somewhat flexible material, both to generate for greater frictional adhesion to the surgeon's fingers. In an alternate embodiment, the loop member can be constructed from a resorbent material such as collagen fabric or Vicryl™ available from Ethicon. Resorbing loop members have an advantage in that they eventually break down and disappear from the implanted wrap. The loop members are open in this embodiment, in part, to reduce the possible build up of bacteria therein. This is of greater concern where resorbent material is not used.

Figure 4:
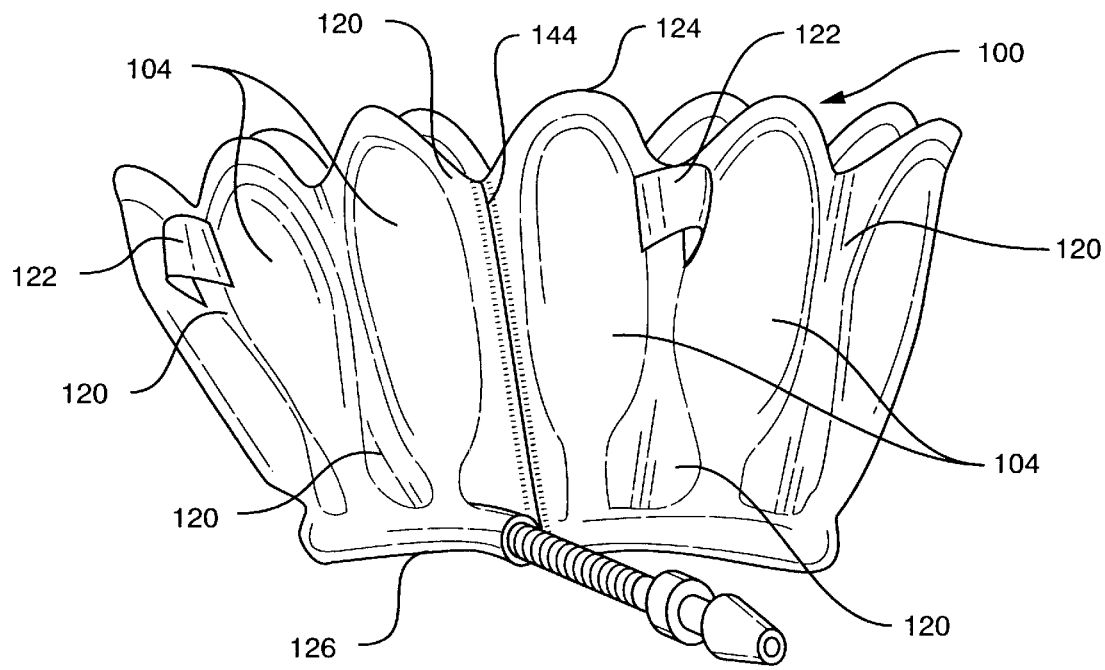
FIG. 4 is a perspective view of the wrap of FIG. 1 in a joined orientation.

Referring briefly to FIG. 4, the wrap is shown in an implanted orientation in which seam 144 is formed by joining opposing free ends of the device together. This joining can be accomplished using clamps, sutures (suture 146 in FIG. 2) or any other suitable joining technique.

Figure 5:
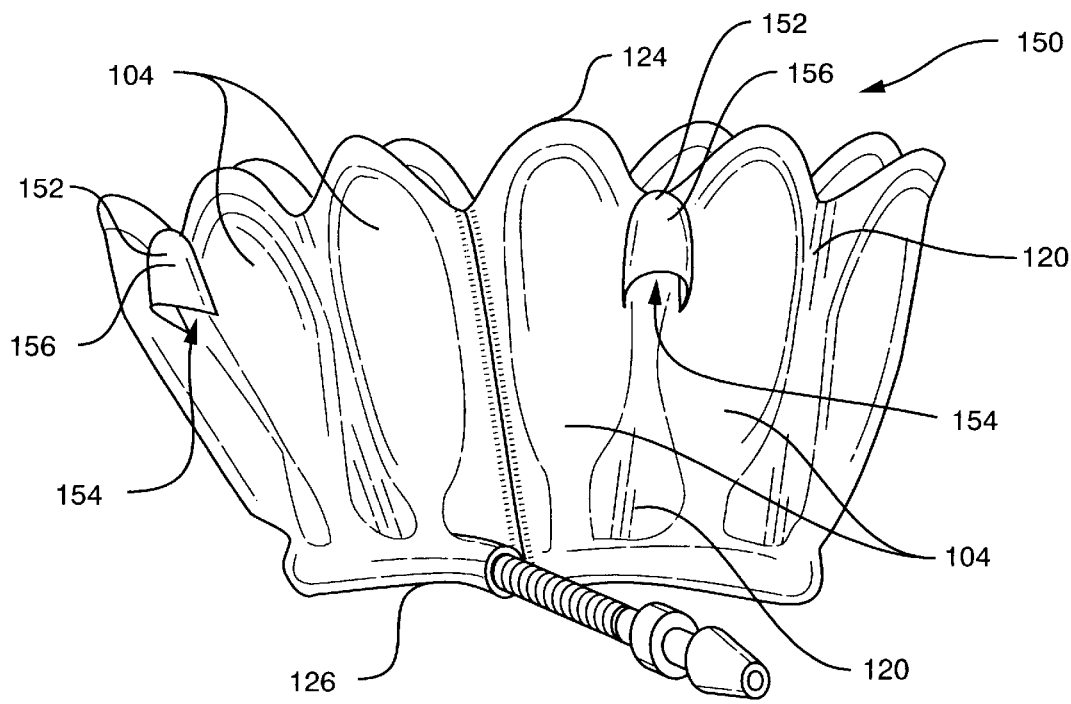
FIG. 5 is a perspective view of an wrap in a joined orientation according to an alternate embodiment.

As noted above, the use of either open loop or closed loop members is contemplated. It is contemplated that either opened or closed loop members can be constructed to seal against the wrap surface after implantation to prevent build-up of biological materials therein; or the loop members can be eliminated by removal (cutting) after implantation is complete or be absorbed back into the body (resorbent material). The wrap 150 of FIG. 5 details enclosed loop members 152 in which the proximal ends 154 thereof are open, and the distal ends 156 are enclosed. A closed loop end further may have an advantage in that the surgeon's fingers are retained at a more predictable point along the wrap as the closed end can act as predictable stops.

Figure 6:
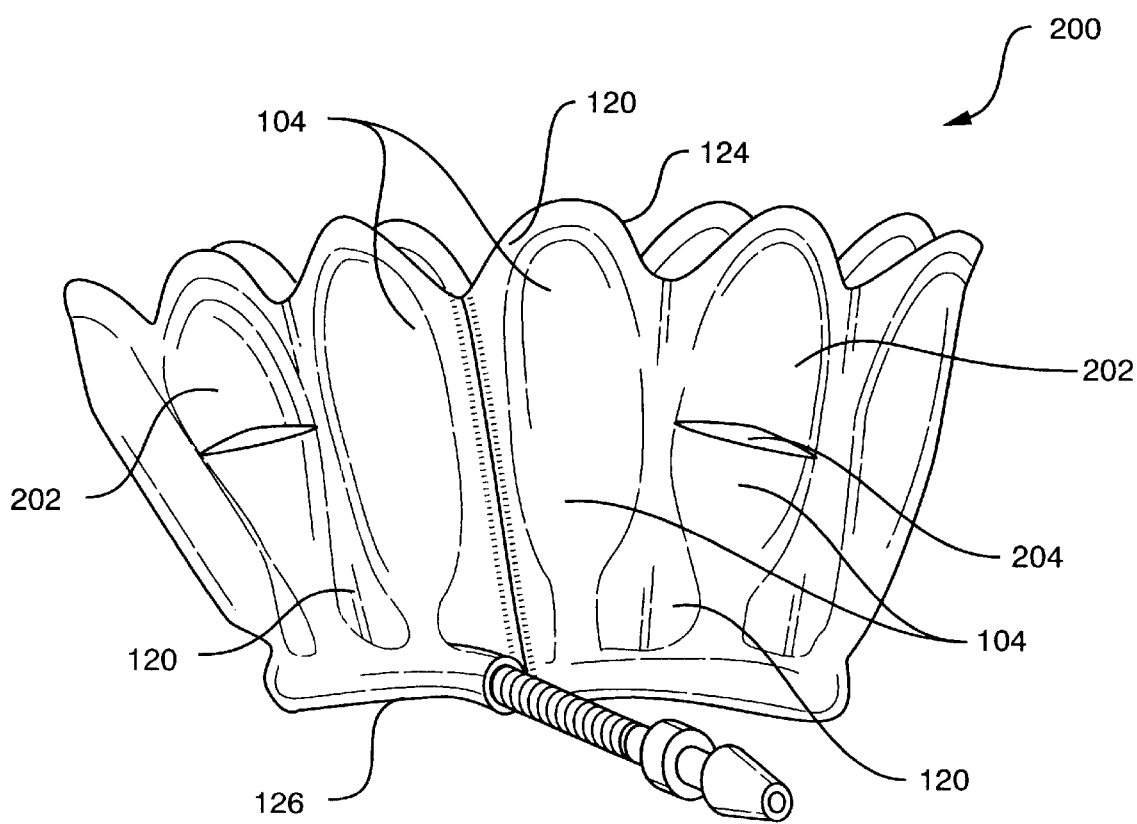
FIG. 6 is a perspective view of an wrap in a joined orientation according to another alternate embodiment.

While the loop members according to FIGS. 1–5 are located in the interstitial sections 120 of the respective wrap, it is contemplated that the balloon pockets can be modified to include a unitary structure for receiving the surgeon's fingers. FIG. 6, therefore, illustrates an wrap 200 in which modified balloon pockets 202 are employed between conventional and enclosed pockets 104. These pockets include a slit 204 that is sufficient in size to accommodate a surgeon's finger therein. Where the wrap is inflatable, the balloons are typically flat enough during implantation to enable the insertion of a finger thereinto. During inflation, the pocket is typically filled substantially by the volume of the balloon, potentially preventing insertion. Since inflation only occurs at the end of the procedure after securing to the heart is complete, there is no restriction to the entry of fingers during the initial part of the implementation process. It is generally desirable that, following implantation, the pockets seal themselves to prevent incursion of contaminants and bacteria. This can be accomplished by an adhesive, sutures, an self-sealing system using, for example, hook and loop technology, or any other acceptable sealing technique that prevents incursion by biological material. In this manner, the risk of bacteriological infection is reduced.

Figure 7:
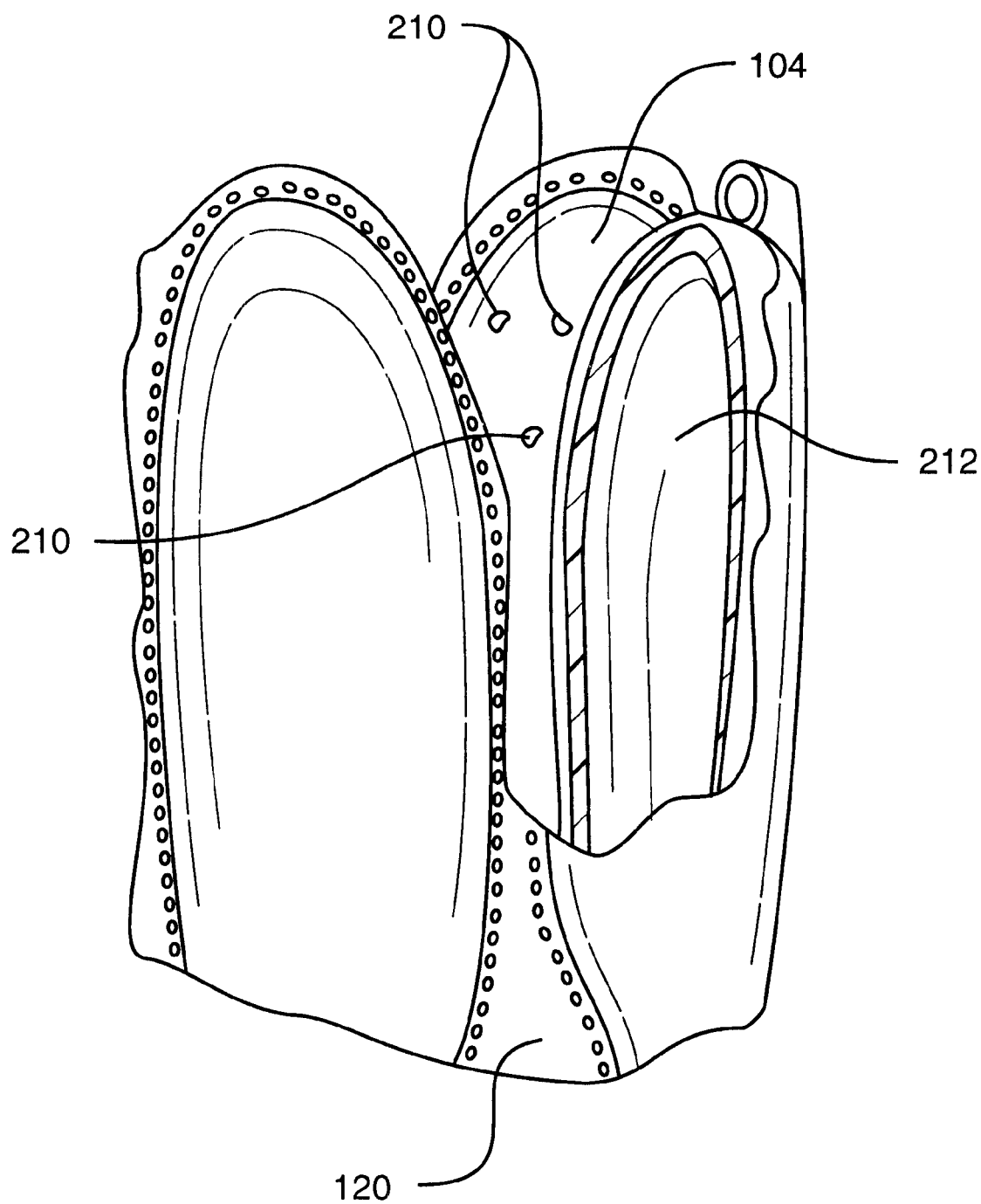
FIG. 7 is a partial cutaway view of an inflatable-balloon-wrap according to this invention.

Referring to FIG. 7, the interior of the wrap according to the various embodiments described herein includes anchoring structures such as microhooks 210 disposed along the interior surface of the wrap, typically along selected balloon pockets. The microhooks can be constructed from any number of biocompatible materials including plastic and metal and are sufficient to anchor the wrap to the surface of the heart free of slippage once the wrap is fully wrapped therearound. The hooks are generally small enough to prevent any significant trauma to the heart wall. Note that the interior of a flexible balloon 212 is also shown for illustration.

Figure 8:
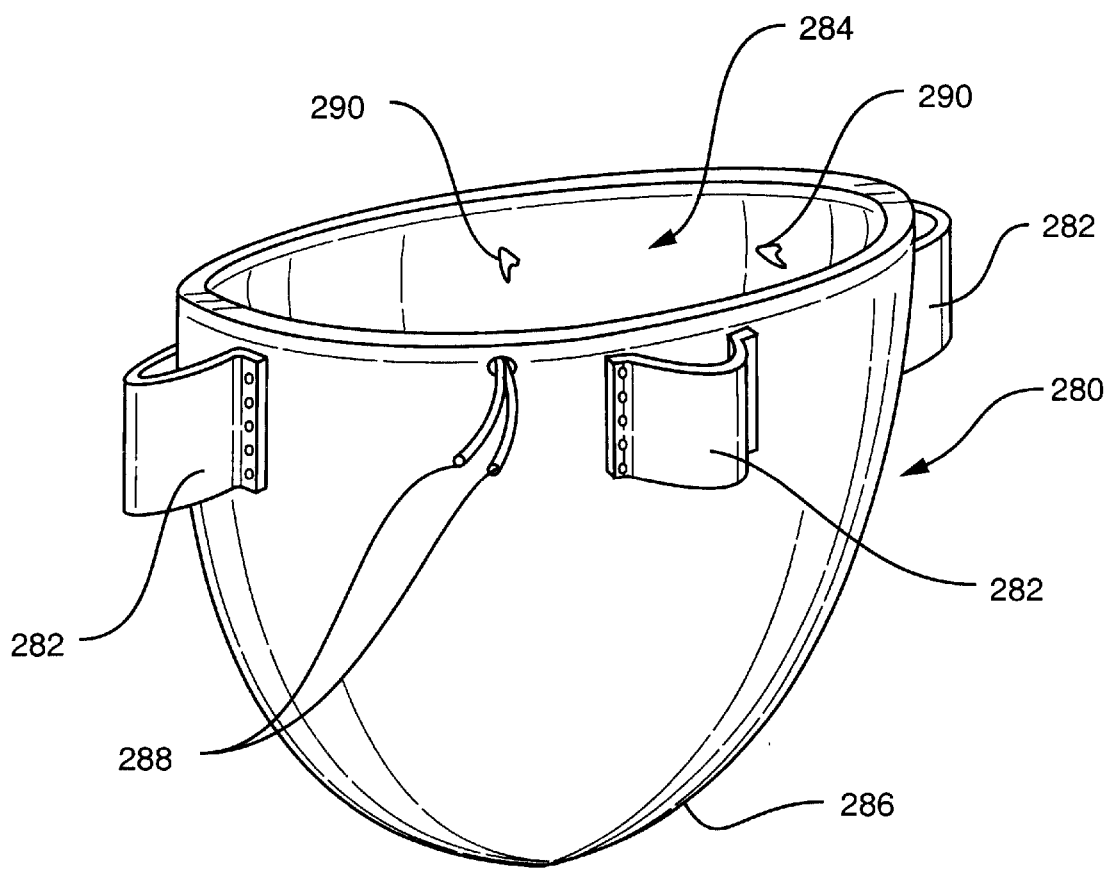
FIG. 8 is a perspective view of a passive girdle-style wrap having engagement members according to an alternate embodiment.

As described above, wrap of this invention can be a closed device (passive or active) rather than a free ends that are secured together during implantation. FIG. 8 illustrates a passive, closed girdle to 80 having a set of open loop members 282 disposed at desired circumfrential positions near the distal end opening 284. In this embodiment, the proximal end 286 is generally closed. Draw strings 288 or other pressure-applying mechanisms can be used to decrease the relative diameter/circumference of the wrap 280. Note that microhooks 290 can, again, be used to secure the wrap's internal wall to the wall of the heart. It is expressly contemplated that any form of loop member/engagement member, including all those described herein, can be used in connection with the closed device. Accordingly, the open loop members 282 are shown by way of example. While the loop members 282 described above are fixed to their respective wrap surfaces, it is expressly contemplated that the loop members can be removable. A most basic form of removability is a system by which stitching or fasteners holding the loop members to their respective wrap services can be quickly detached by cutting, untying or by otherwise actuating an appropriate release element (e.g., pulling a thread). Similarly, the loop members can be arranged for easy removal by cutting with surgical scissors or a scalpel. In another embodiment, loop members can be constructed from an elastic material that lays essentially flat against the surface after fingers are withdrawn. In this embodiment, the surgeon would typically be required to insert his or her fingers over the elastic loop members before implantation.

Figure 9:
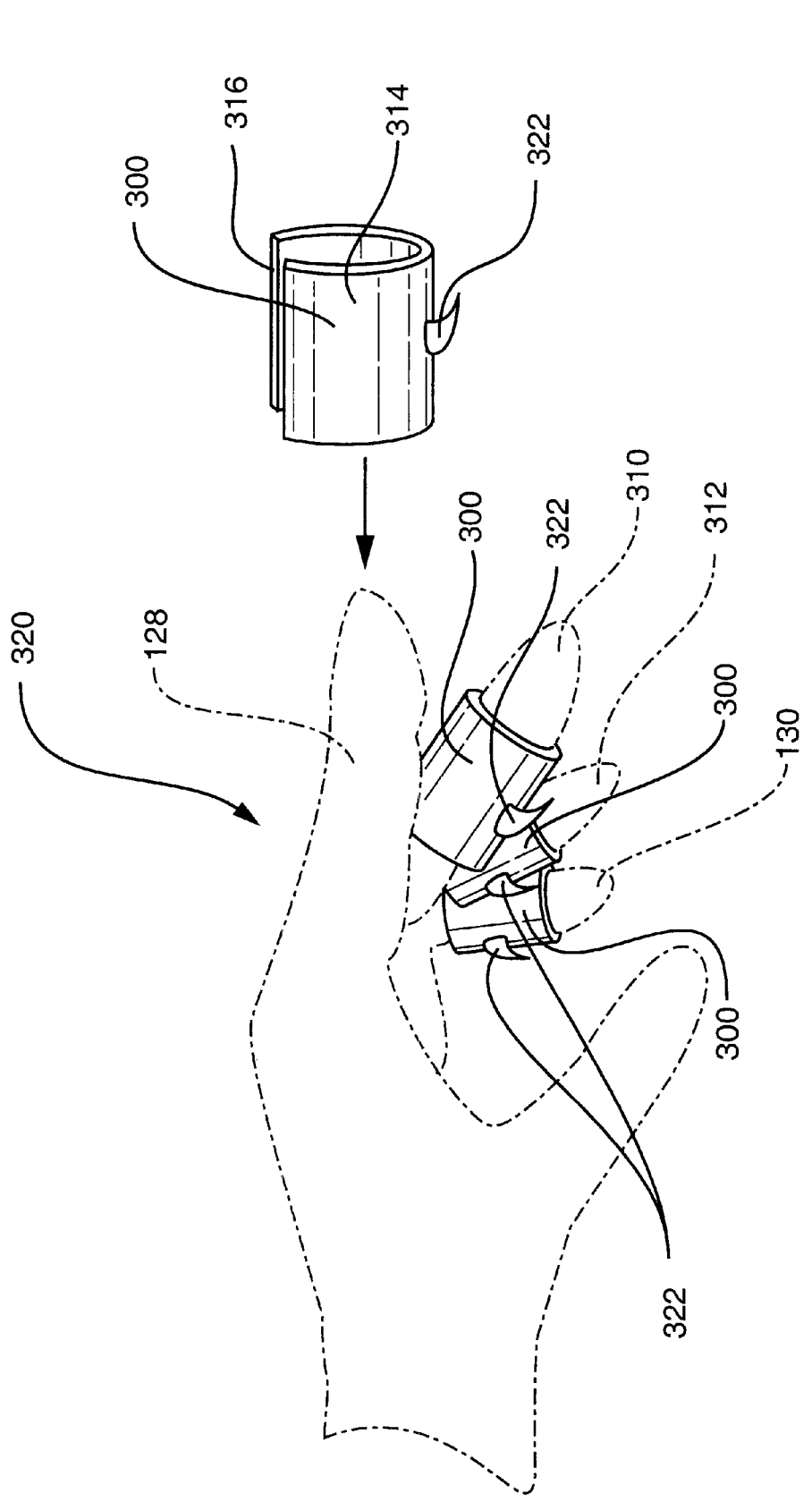
FIG. 9 is a side perspective view of a set of detachable engagement members according to an alternate embodiment.

FIG. 9 illustrates an alternate embodiment in which loop members 300 are removeably secured to one or more of the surgeon's fingers 128, 130, 310 and 312. Each of the loop members can be sized similarly, or can be custom sized to the particular finger. The loop members 300 comprise a barrel assembly 314 that, in this embodiment has an open split 316 for varying the diameter and pressure applied by the loop member on the underlying surgical glove 320. The ring 314 can comprise a sterile material, such as a suitable plastic or metal. It provides sufficient pressure to clip securely onto an appropriate location of each finger. The friction provided by the glove 320 assists in securing each ring. Each ring includes a hook or pin 322 that, in this embodiment, is directed forwardly away from the hand (e.g., in a distal direction with respect to the wrap). The hook can be located at any position along the respective ring 314. It can define a variety of shapes. The loop members 300 can be preapplied to the wrap, and then attached to the surgeon's fingers before implantation, or can be first attached to the surgeon's fingers and then applied to the surface of the wrap.

Figure 10:
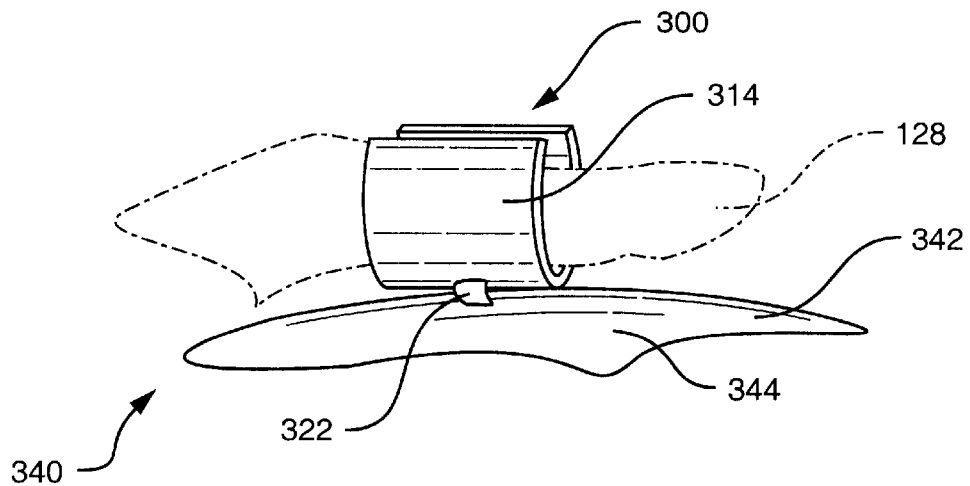
FIG. 10 is a side view of one of the engagement members of the FIG. 9 shown engaged to the surface of an wrap.

In FIG. 10, the loop member is shown with its hook inserted into the wrap surface 340. Typically, at least two plies of material are used in the wrap (for example in the interstitial section 120 in FIGS. 1–5). The hook passes through the upper ply 342 but remains above the lower ply 344 so that it does not contact the outer wall of the heart. A special pocket can also be provided for receiving the hook 322 above the other structural plies 342 and 344 of the wrap. Note that the tip of the hook, engaging the wrap surface can be sufficiently blunted so as to avoid puncturing a balloon.

Figure 11:
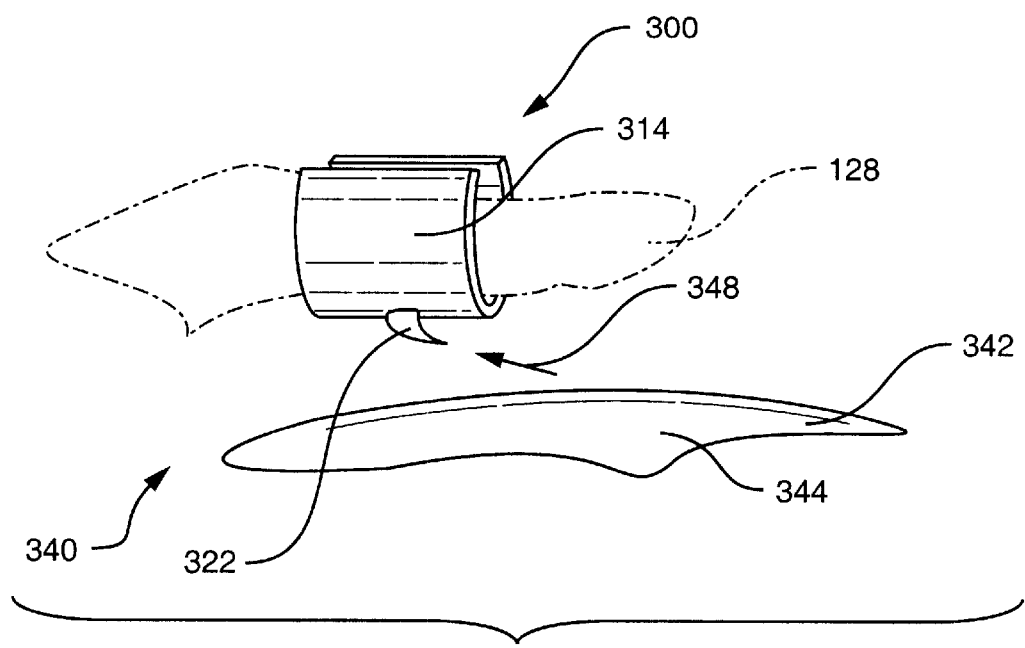
FIG. 11 is a side view of the engagement member and service of FIG. 10 shown in relative disengagement.

As shown in FIG. 11, upon removal the hook withdraws (arrow 348) from the surface 340 allowing the plies 342 and 344 to come together. The hook, in this embodiment, is barbless so that is does not substantially resist removal in the proximal direction. It is oriented to enable motion in the distal direction to direct the wrap onto the heart and also, in a lateral direction transverse to the distal direction. It can be shaped so that minimal movement in the proximal direction is also permitted. However, given the proper combination of proximal and upward motion, such as that shown by the arrow 348, the loop member 300 is relatively easily removed from the surface 340.

Figure 12:
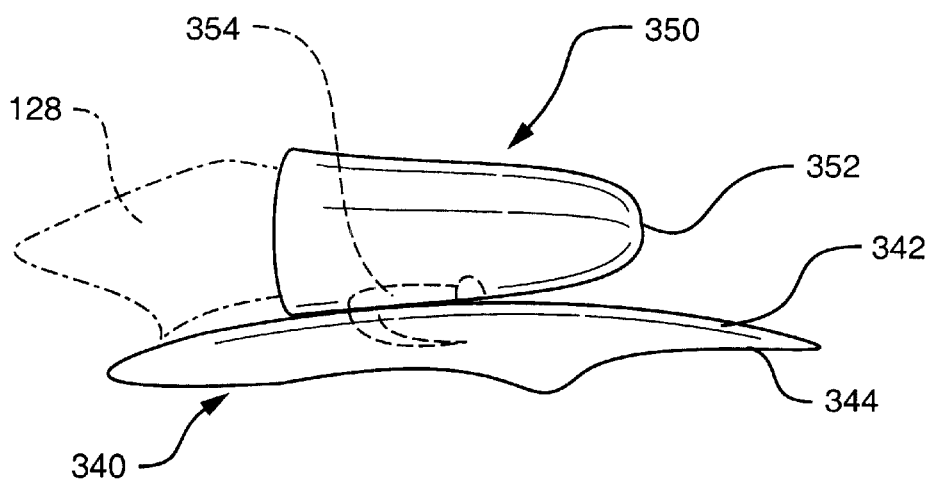
FIG. 12 is a side view of an alternate embodiment of an engagement member shown engaged to the surface of a wrap.
Figure 13:
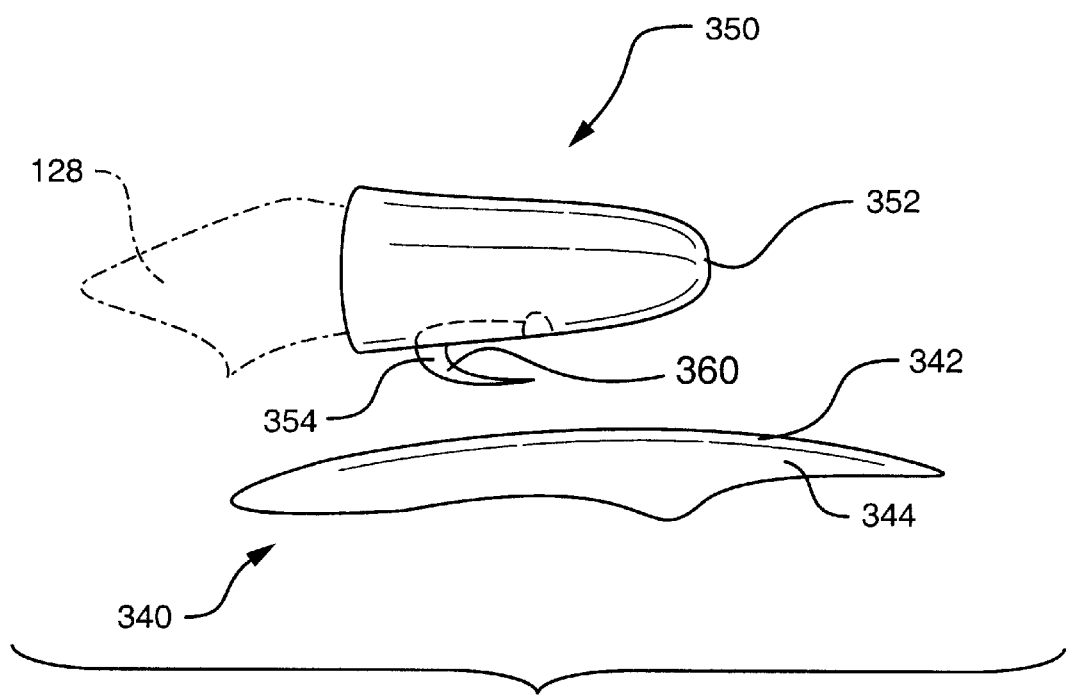
FIG. 13 is a side view of the engagement member and surface of FIG. 12 shown in relative disengagement.

FIG. 12 shows an alternate embodiment of a removable loop member 350. The loop member 350 comprises a loop of cloth. In this embodiment, it is a closed loop that covers the tip of the finger with a corresponding distal closure 352. However, an open loop having a desired taper can also be used. Additionally, while fabric is employed, it is also contemplated that the loop member 350 can be constructed from a ridged or semi-rigid material in the manner of a thimble. A hook structure 354 is anchored onto a bottom side of the loop member 350. The hook is directed in a distal direction to, again, engage the surface 340 of the wrap between plies 342 and 344. Upon withdrawal, as shown in FIG. 13, the hook pulls free (arrow 360) of the surface 340 leaving an uncluttered wrap surface following completion of the implantation process.

Figure 14:
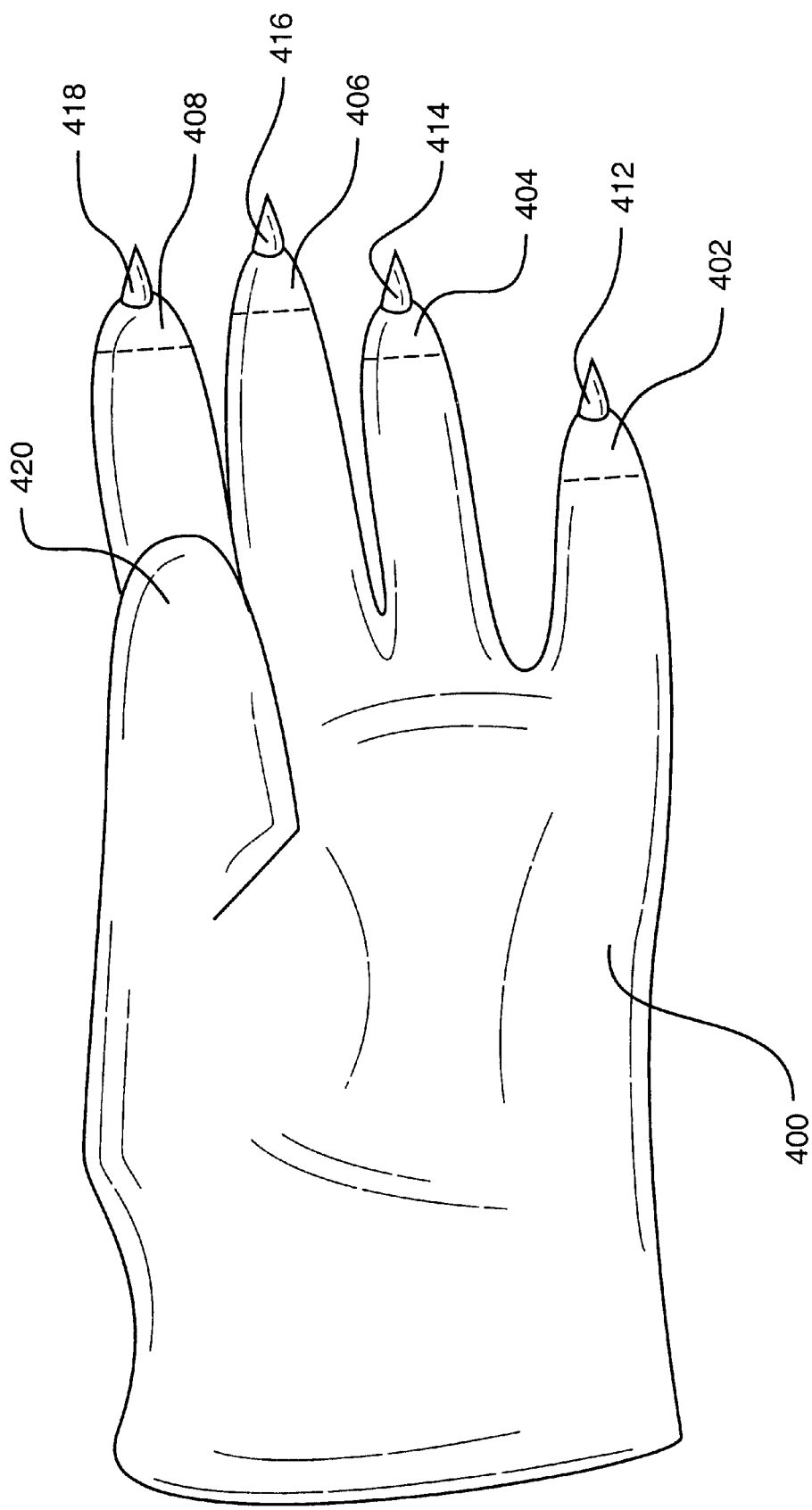
FIG. 14 is a surgical glove having integral engagement members mounted thereon according to an alternate embodiment.

FIG. 14 details another alternate embodiment in which the fingers of a surgical glove 400 act as loop members. Each finger 402, 404, 406 and 408 includes a respective point or hook 412, 414, 416 and 418. The thumb 420 of the glove is typically free of any hook or point. The hooks or points 412, 414, 416, 418 engage special pockets (not shown) or the plies of the wrap surface to assist in directing it to the implant site of the heart. The shape of the points or hooks can be varied. Somewhat blunted points, as shown, can be used. Conversely, sharper points can be provided, particularly where the points are to be inserted into an unbroken material ply. The fingers can also include reinforcing sections shown generally by the dotted lines. The reinforcing material can be rigid or semirigid and is generally integral with the overall glove 400.

Figure 15:
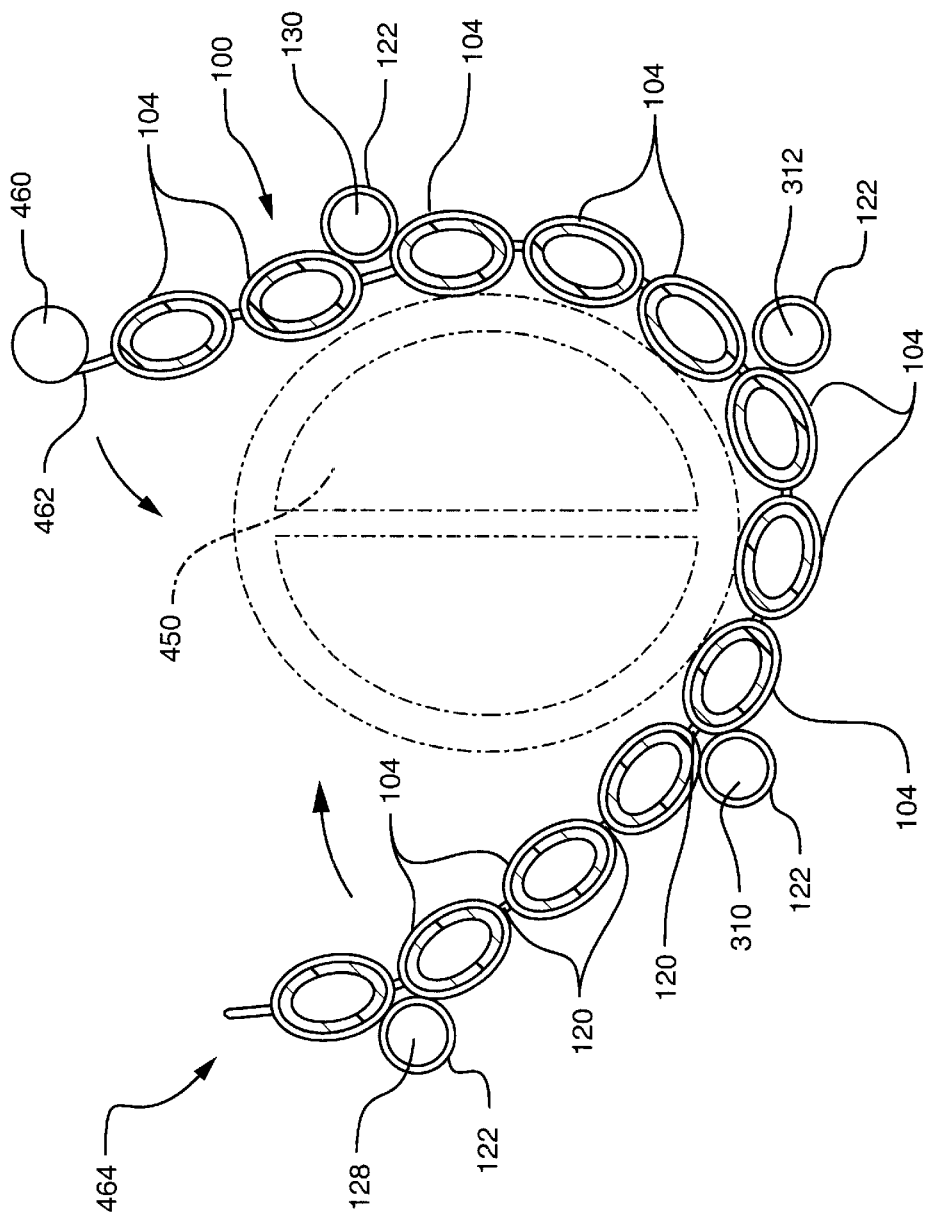
FIG. 15 is a somewhat schematic cross section showing the wrapping of an wrap according to an embodiment of this invention around an exemplary heart.
Figure 16:
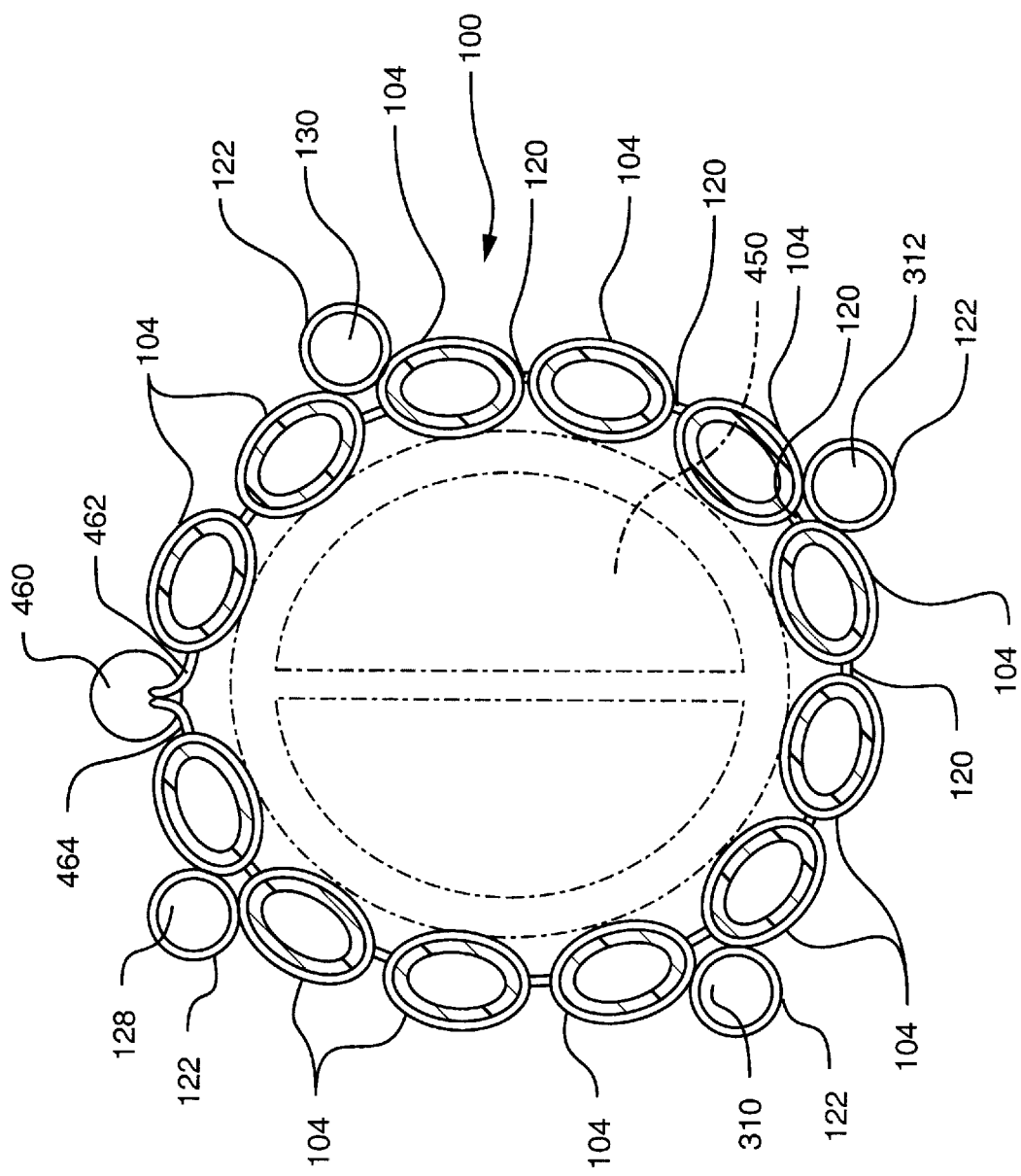
FIG. 16 is a somewhat schematic cross section showing the fitting of the wrap wrapped in FIG. 15 to the heart.
Figure 17:
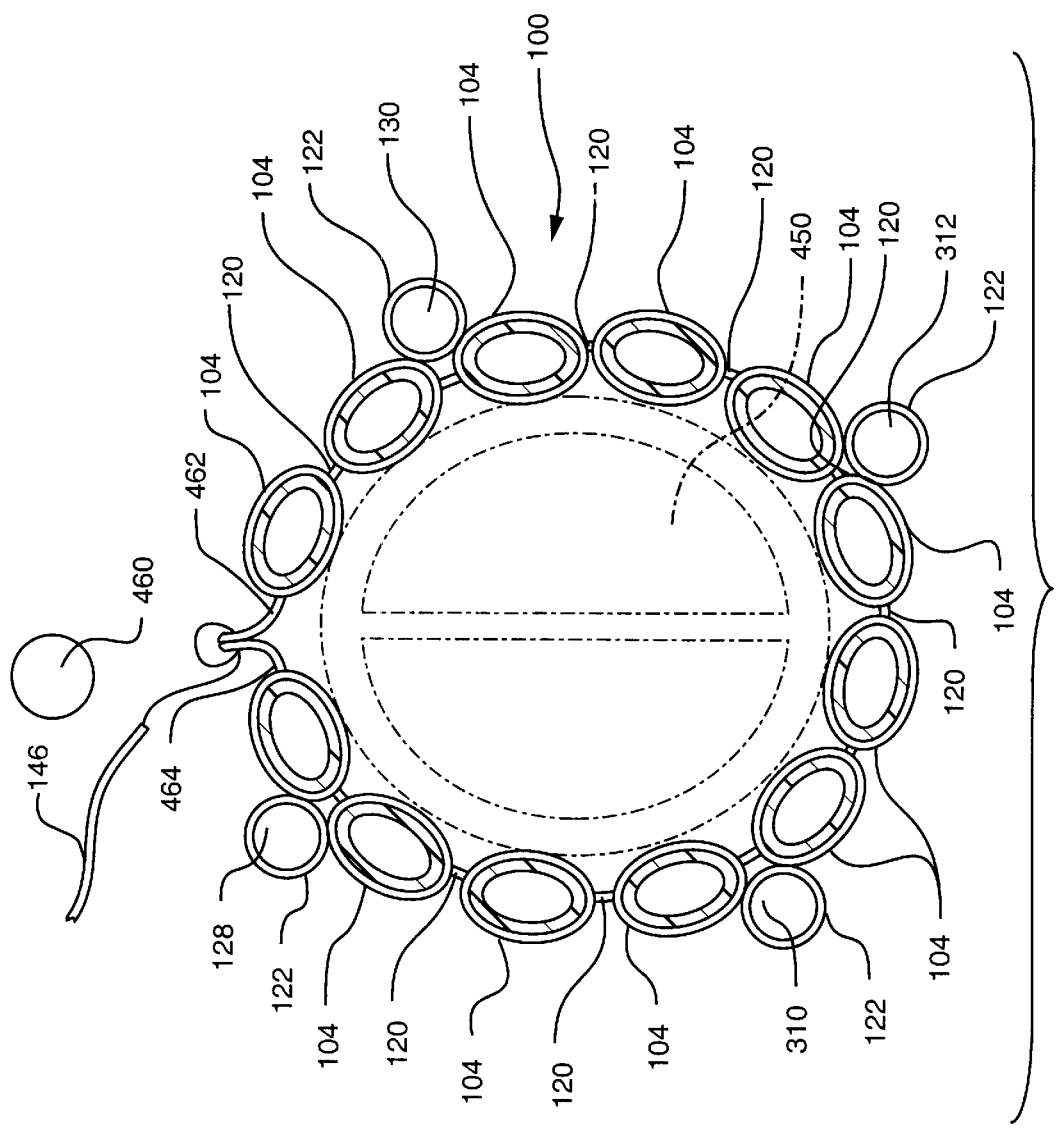
FIG. 17 is a somewhat schematic cross section showing the securing of the wrap of FIGS. 16 and 17 into a final position around the heart.

FIGS. 15–17 show an exemplary implantation process involving a wrap according to the embodiment of FIGS. 1–4. While not shown, the patient is initially prepared for the implantation of the wrap by performing an incision in the thoracic region within the fifth intercostal space. The resulting thoracotomy is performed using a relatively small incision in comparison to prior implantation procedures. The patient's overlying lung is then moved aside and retained to expose the heart beneath. Next, the pericardium is incised and/or removed to provide direct access the heart. The heart is then lifted to expose the ventricular region while the surgeon's left hand engages the loop members 122 with his or her fingers 128 and 130, 310 and 312 to form the wrap into an implantable geometry that enables it to be placed adjacent to the heart and subsequently pass around the heart. The surgeon applies the wrap over the ventricular region of the heart as shown. The heart is typically lowered after the wrap is in engagement with the ventricular region. The thumb 460 remains free, prepared to hold down the two free ends 462 and 464 of the wrap. Typically, the left hand is used to hold the wrap. Accordingly, the loop members are arranged specifically to accommodate the left hand while the right hand is used to secure the wrap as described further below. While the wrap and associated loop members are adapted to be engaged by a left hand, it expressly contemplated that right-hand engagement can be employed in an alternate embodiment.

According to FIG. 16, the surgeon fully encircles the heart 450 and places his or her thumb 460 on each of the ends 462 and 464 to retain them in a desired overlapping relationship. The ends are thus held in place against the heart with the assistance of the microhooks, until the ends 462 and 464 can be joined.

The free ends 462 and 464 of the wrap are joined together according to FIG. 17. In this example, a suture 146 is used to sew the ends together in an appropriate orientation. By maintaining close hand engagement with the wrap at all times during the implantation, the surgeon develops a very accurate feel for the location and orientation of the wrap. The fingers act as individual "clamps" during the procedure. These clamps have the added ability of providing valuable tactile feedback in addition, the surgeon using his or her fingers in close proximity to the heart can manipulate the wrap into a more-optimum shape prior to securing with, for example, the suture 470. For example, the ends 462 and 464 may desirably overlap each other at an angle to vary the conical angle of the wrap between its proximal end and distal end so that it better matches the unique cone-shape of the affected heart. Furthermore, one end may be located higher than the other end to apply pressure "higher up" on, for example, the left ventricle of the heart.

Once the free ends 462 and 464 have been appropriately secured, the surgeon's hand is withdrawn and, if appropriate the loop members are removed. Also if appropriate, the balloons are inflated to provide an appropriate pressure and/or they are connected to a reciprocating pumping mechanism that assists the hearts own pump action through expansion and contraction of the balloons.

The foregoing has been a detailed description of preferred embodiments of the invention. Various modifications and additions can be made without departing from the spirit and scope of this invention. For example, while the wrap of this invention is adapted for engagement by a surgeon's fingers, various robotic manipulators that perform the general motion of fingers can be substituted wraps can be secured to the wall of the heart by a variety of techniques other than microhooks. The number and arrangement of material plies and seams can be widely varied. In addition, the internal strengthening and/or pressure-generating members of the wrap can be widely varied. For example, a series of longitudinal balloon rings can be provided instead of the vertically oriented balloons shown and described herein. Other forms of pressure-generating and/or stiffening members can also be used within the structure of the wrap. Accordingly, this description is meant to be taken only by way of example, and not to otherwise limit the scope of the invention.

What is claimed is:

1. A system for treating an affected organ of a patient comprising:
    an engagement member adapted to removably engage a clinician's hand until a predetermined disengagement time, the engagement member being operatively connected to an implantable wrap to provide tactile control of wrap placement during implantation.

2. The system as set forth in claim 1 wherein the engagement member comprises a loop member adapted to extend substantially around a portion of the finger of the hand to removably restrain the finger with respect to the wrap.

3. The system set forth in claim 2 wherein the loop member comprises a fabric loop attached to a surface of the wrap.

4. The system as set forth in claim 2 wherein the loop member includes a proximal end adapted to receive the finger therein and a distal end remote from the proximal end, the proximal end being wider than the distal end to thereby define a taper for restraining the finger against forward movement beyond a predetermined position within the loop.

5. The system as set forth in claim 2 further comprising a plurality of loop members located at predetermined positions about a circumference of the wrap for engaging each of a plurality of fingers of the hand.

6. The system as set forth in claim 2 wherein the loop member comprises a material capable of being absorbed by a human body.

7. A system for treating an affected organ of a patient comprising:
    an implantable wrap;
    an engagement member adapted to removably engage a clinician's hand until a predetermined disengagement time, the engagement member being operatively connected to the implantable wrap;
    the engagement member comprising a loop member adapted to extend substantially around a portion of a finger of the hand to removably restrain the finger with respect to the wrap;
    wherein the loop includes a proximal end for receiving the finger and a distal end remote from the proximal end, the distal end being enclosed to prevent movement of the finger therethrough.

8. A system for treating an affected organ of a patient comprising:
    an implantable wrap;
    an engagement member adapted to removably engage a clinician's hand until a predetermined disengagement time, the engagement member being operatively connected to the implantable wrap;
    the engagement member comprising a loop member adapted to extend substantially around a portion of a finger of the hand to removably restrain the finger with respect to the wrap;
    wherein the wrap includes at least two plies of material overlaid atop each other and wherein the loop is defined by a slit in an outer ply of the two plies of material constructed and arranged to receive the finger there into.

9. The system as set forth in claim 8 wherein the slit is located on a pocket for holding an inflatable balloon.

10. A system for treating an affected organ of a patient comprising:
    an implantable wrap;
    an engagement member adapted to removably engage a clinician's hand until a predetermined disengagement time, the engagement member being operatively connected to implantable wrap;
    the engagement member comprising a loop member adapted to extend substantially around a portion of a finger of the hand to removably restrain the finger with respect to the wrap; and
    a removable base attached to the loop, the base being constructed and arranged so that the loop is removable from the wrap upon application of a predetermined motion thereto in a predetermined direction.

11. The system as set forth in claim 10 wherein the base comprises a pin adapted for insertion into a portion of the wrap.

12. The system as set forth in claim 10 wherein the loop comprises a finger of a glove and the base is attached thereto.

13. A system for treating an affected organ of a patient comprising:
    an implantable wrap;
    an engagement member adapted to removably engage a clinician's hand until a predetermined disengagement time, the engagement member being operatively connected to the implantable wrap;
    the engagement member comprising a plurality of loop members located at predetermined positions about a circumference of the wrap for engaging each of a plurality of fingers of the hand;
    each loop member adapted to extend substantially around a portion of a finger to removably restrain the finger with respect to the wrap;
    wherein the wrap includes a pair of free ends and wherein each of the loops are positioned so that a thumb of the hand can be placed over the ends when the free ends are joined together with the wrap in a wrapped orientation around a heart.

14. A method for implanting a cardiac wrap on a heart comprising:
    mounting selected fingers of a clinician's hand to engagement members interconnected with the wrap so as to maintain the fingers in tactile control of wrap placement during implantation until a predetermined time;

moving the wrap into a geometry adapted for implanting the wrap with respect to the heart through a chest incision proximate to the heart;

locating the wrap at an implanted position with respect to the heart;

affixing the wrap in the implanted position on the heart; and at the predetermined time performing a detachment motion so as to detach the selected fingers from engagement with the wrap.

15. A method for implanting a cardiac wrap on a heart comprising:

mounting selected fingers of a clinician's hand to engagement members interconnected with the wrap so as to engage the fingers with the wrap until a predetermined time;

moving the wrap into a geometry adapted for implanting the wrap with respect to the heart through a chest incision proximate to the heart;

locating the wrap at an implanted position with respect to the heart;

affixing the wrap in the implanted position on the heart; and at the predetermined time performing a detachment motion so as to disengage the selected fingers from the wrap;

wherein the step of mounting comprises inserting the selected fingers into loop members attached to a surface of the wrap at predetermined locations about a circumference thereof.

16. A method for implanting a cardiac wrap on a heart comprising:

mounting selected fingers of a clinician's hand to engagement members interconnected with the wrap so as to engage the fingers with the wrap until a predetermined time;

moving the wrap into a geometry adapted for implanting the wrap with respect to the heart through a chest incision proximate to the heart;

locating the wrap at an implanted position with respect to the heart;

affixing the wrap in the implanted position on the heart; and at the predetermined time performing a detachment motion so as to disengage the selected fingers from the wrap;

wherein the step of detaching comprises removing the selected fingers from the loop members.

17. A method for implanting a cardiac wrap on a heart comprising:

mounting selected fingers of a clinician's hand to engagement members interconnected with the wrap so as to engage the fingers with the wrap until a predetermined time;

moving the wrap into a geometry adapted for implanting the wrap with respect to the heart through a chest incision proximate to the heart;

locating the wrap at an implanted position with respect to the heart;

affixing the wrap in the implanted position on the heart; and at the predetermined time performing a detachment motion so as to disengage the selected fingers from the wrap;

wherein the step of detaching comprises removing the loop members from the wrap based upon a predetermined detachment motion.

18. A method for implanting a cardiac wrap on a heart comprising:

mounting selected fingers of a clinician's hand to engagement members interconnected with the wrap so as to engage the fingers with the wrap until a predetermined time;

moving the wrap into a geometry adapted for implanting the wrap with respect to the heart through a chest incision proximate to the heart;

locating the wrap at an implanted position with respect to the heart;

affixing the wrap in the implanted position on the heart; and at the predetermined time performing a detachment motion so as to disengage the selected fingers from the wrap;

wherein the step of affixing includes moving the selected fingers so as to place opposing free ends of the wrap in an overlapping relationship and applying securing members to maintain the free ends in the overlapping relationship.

19. The method is set forth in claim 18 wherein the step of affixing includes holding the free ends together in the overlapping relationship while the securing members are applied to the free ends.

20. An apparatus for treating a heart comprising:

a cardiac wrap constructed and arranged to apply pressure about a portion of a circumference of the heart; and a plurality of finger-engaging loops located at predetermined positions on a surface of the wrap so that a hand has tactile control of wrap placement during implantation on the heart, the loops adapted to apply friction to respective fingers inserted thereinto to maintain engagement therebetween.

21. A cardiac wrap adapted to apply pressure about a portion of a circumference of a heart when the wrap is in engagement with the heart comprising:

a wrap body having an inner surface adapted to engage the heart and an opposing outer surface; and a plurality of material loops each attached to at least two locations along the outer surface so as to define openings that receive fingers of a hand, wherein the hand is movable to place the wrap into an enclosing relationship around the heart.

22. The cardiac wrap as set forth in claim 21 wherein the wrap body includes a plurality of inflatable elements between the inner surface and the outer surface for applying variable pressure to the heart based upon an amount of fluid present in the balloons.

23. The cardiac wrap as set forth in claim 21 wherein the wrap body defines an upper edge and a lower edge opposite the upper edge, the lower edge adapted to be more remote from major blood vessels of the heart than the upper edge when the wrap is in engagement with the heart, and each of the material loops being located adjacent the upper edge of the wrap.

24. The cardiac wrap as set forth in claim 23 wherein each of the material loops defines a first loop edge adjacent the upper edge of the wrap body and a second loop edge remote from the upper edge of the wrap body and wherein the first loop edge defines a first loop opening and the second loop edge defines a second loop opening.

25. The cardiac wrap as set forth in claim 24 wherein the first loop opening is smaller than the second loop opening so as to resist passage of a finger from the second loop opening through the first loop opening.

26. The cardiac wrap as set forth in claim 23 wherein each of the material loops defines a first loop edge adjacent the upper edge of the wrap body and a second loop edge remote from the upper edge of the wrap body wherein the second loop edge defines a loop opening sized to allow a finger to pass therethrough and wherein the first loop edge is sealed against the wrap body.

27. The cardiac wrap as set forth in claim 21 wherein each of the material loops is joined to the wrap body at two-spaced apart locations by seams that include securing thread.

28. A method for implanting a cardiac wrap having a wrap body adapted to enclose a portion of a circumference of a heart comprising:

engaging the wrap body with a hand, including placing fingers of the hand within each of a plurality of material loops attached along an outer surface of the wrap body and forming a cup-shape with the wrap;

passing the wrap body over a ventricular region of the heart and positioning the wrap body at a desired location around the circumference of the heart;

securing free ends of the wrap body together so that the wrap body defines a predetermined circumference; and removing the fingers from the material loops.

29. The method as set forth in claim 28 further comprising detaching the material loops after the fingers are removed therefrom.

30. The method as set forth in claim 28 wherein the step of detaching includes cutting the material loops at locations on the loops adjacent the outer surface of the wrap body.

31. The method as set forth in claim 28 wherein the step of placing the fingers within each of the material loops includes passing fingers into respective openings in the material loops until each of the fingers is resisted by an increasing taper defined in each of the material loops.

32. A cardiac wrap adapted to apply pressure about a portion of a circumference of a heart when the wrap is in engagement with the heart comprising:

a wrap body having an inner surface adapted to engage the heart and an opposing outer surface; and a plurality of pockets defined on the outer surface, the pockets being sized and arranged so that respective fingers can pass thereinto, each of the pockets including a first end defining an opening for receiving each of the fingers, respectively, and a second end that is closed against the wrap body to resist movement of each of the fingers, respectively.

33. The cardiac wrap as set forth in claim 32 wherein the outer surface comprises an outer surface material layer and wherein each of the pockets are defined by a portion of the outer surface material layer, the first end of each of the pockets being a separation of the portion of the outer surface material layer for a surrounding region of the outer surface material.

34. The cardiac wrap as set forth in claim 33 wherein the first edge is constructed an arranged to be sealed against the wrap body so as to close the opening at a predetermined time.

35. The cardiac wrap as set forth in claim 32 further comprising a plurality of inflation elements that expand and contract in response to a level of fluid therein, each of the plurality of inflation elements including a balloon disposed between the inner surface and the outer surface.

36. The cardiac wrap as forth in claim 35 wherein each of the pockets is located between a respective pair of the plurality of inflation elements.

37. A cardiac wrap adapted to apply pressure about a portion of a circumference of a heart when the wrap is in engagement with the heart comprising:

a wrap body having an inner surface adapted to engage the heart and an opposing outer surface; and a plurality of removable loop members adapted to engage fingers of a hand, the loop members being attached to the outer surface so that the loop members remain engaged to the outer surface to provide tactile control of wrap placement as an implanting force is applied in a first direction that can move the wrap over a ventricular region of the heart, toward major blood vessels of the heart, onto a predetermined location thereon.

38. The cardiac wrap as set forth in claim 37 wherein the plurality of removable loop members include hook elements that selectively engage the outer surface when force is applied to the plurality of removable loop members in the first direction and that, alternatively disengage in the outer surface when force is applied in an opposing second direction.

39. The cardiac wrap as set forth in claim 38 wherein the plurality of removable loop members comprise semi-rigid ring elements adapted to frictionally engage tips of the fingers.

40. The cardiac wrap as set forth in claim 38 wherein the semi-rigid ring elements define a split adapted to enable the rigid members to flex about the fingers.

41. The cardiac wrap as set forth in claim 38 wherein the plurality of removable loop members comprise enclosed structures having an opening at one end for receiving fingers thereinto and an enclosed tip at an opposing end for resisting passage of fingers therethrough.

42. A cardiac wrap as set forth in claim 38 wherein the hooks are mounted on each of the plurality of removable loop members, respectively, and the hooks are adapted to be removed, respectively, from the outer surface of the wrap body in conjunction with each of the plurality of removable loop members.

43. The cardiac wrap as set forth in claim 38 wherein the hooks are fixedly mounted to predetermined locations on the outer surface of the wrap body and the plurality of removable loop members are each adapted to disengage from the hooks when force is applied in the second direction to each of the loop members.

44. A system for implanting a cardiac wrap adapted to apply pressure about a portion of a circumference of a heart when the wrap is in engagement with the heart comprising:

a wrap body having an inner surface adapted to engage the heart and an opposing outer surface; and a glove having fingers, each finger of the glove including one of a hook and a spike for engaging the outer surface so as to grip the outer surface when pressure is applied in a first direction to pass the wrap over a ventricular region of the heart, toward major blood vessels.

45. The system as set forth in claim 44 wherein the wrap body includes a pair of free ends adapted to be joined when the wrap body is in engagement with the heart so as to define a predetermined circumference of the wrap body in engagement with the heart.

46. The system as set forth in claim 44 wherein the wrap body includes a plurality of inflation elements that expand and contract in response to an amount of fluid therein.

47. A method for implanting a cardiac wrap that applies pressure about a portion of a circumference of a heart comprising:

engaging, with fingers of a hand, a plurality of finger engaging members;

applying a plurality of finger-engaging members to a wrap body so that the finger engaging members remain removably attached to the wrap body while a force is applied by the hand in a first direction toward major blood vessels to implant the wrap over a ventricular region of the heart; and disengaging the hand from the wrap body so that the plurality of finger-engaging members remain attached the fingers when a force is applied is a second opposing direction from the first direction by the hand.

48. The method as set forth in claim 47 wherein the step of applying includes passing the plurality of finger-engaging members over hooks fixedly attached to the wrap.

49. The method as set forth in claim 47 wherein the step of applying includes directing respective pointed members on each of the plurality of finger-engaging members into the wrap body in the first direction so as to engage the wrap body.

* * * * *

UNITED STATES PATENT AND TRADEMARK OFFICE
CERTIFICATE OF CORRECTION

PATENT NO. : 6,572,534 B1
DATED : June 3, 2003
INVENTOR(S) : Michael T. Milbocker and Robert L. Buck It is certified that error appears in the above-identified patent and that said Letters Patent is hereby corrected as shown below:

Column 9,
Between lines 29 and 30, insert -- "an implantable wrap; and" --
Line 34, "an" should read -- "the" --

Column 10,
Line 30, between "to" and "implantable" insert -- "the" --

Column 13,
Line 63, "an" should read -- "and" --

Column 14,
Line 4, between "as" and "forth" insert -- "set" --

Column 16,
Line 1, "the fingers when a force is applied is a second opposing:" should read -- "to the fingers when a force is applied in a second opposing" --

Signed and Sealed this

Twenty-fourth Day of August, 2004

JON W. DUDAS
*Director of the United States Patent and Trademark Office*